(12) United States Patent
Bilginturan et al.

(10) Patent No.: US 6,248,873 B1
(45) Date of Patent: Jun. 19, 2001

(54) HYPERTONIA GENE

(75) Inventors: Nihat Bilginturan, Ankara (TR); Sylvia Bähring, Berlin-Buch (DE); Friedrich Luft, Berlin-Buch (DE); Herbert Schuster, Berlin-Buch (DE); Thomas Wienker, Berlin-Buch (DE)

(73) Assignee: Progen Biotechnik GmbH, Heidelberg (DE)

( * ) Notice: Subject to any disclaimer, the term of this patent is extended or adjusted under 35 U.S.C. 154(b) by 0 days.

(21) Appl. No.: 09/155,756
(22) PCT Filed: Apr. 4, 1997
(86) PCT No.: PCT/DE97/00700
§ 371 Date: Feb. 5, 1999
§ 102(e) Date: Feb. 5, 1999
(87) PCT Pub. No.: WO97/38082
PCT Pub. Date: Oct. 16, 1997

(30) Foreign Application Priority Data

Apr. 4, 1996 (DE) ................................. 196 13 606

(51) Int. Cl.$^7$ .................................. C07H 17/00
(52) U.S. Cl. ............................................ 536/23.1
(58) Field of Search ............................. 536/23.1

(56) References Cited

FOREIGN PATENT DOCUMENTS

WO 94/08048A   4/1994  (WO) .

OTHER PUBLICATIONS

Albertson et al., "Construction and Characterization of a yeast artificial chromosome library containing seven haploid human genome equivalents", *Proc. Natl. Acad. Sci. USA* 87:4256–4260 (1990).

Baehring et al., "Construction of a physical map and additional phenotyping in autosomal dominant hypertension and brachydactyly, which maps to chromosome 12", *American Journal of Human Genetics*, Bd 59 No. 4 (Supp), (1996).

Bilginturan et al., "Hereditary brachydactyly associated with hypertension", *Journal of Medical Genetics* 10:253–259 (1973).

Frossard et al., "Association between a dimorphic site on chromosome 12 and clinical diagnosis of hypertension in three independent populations" *Clinical Genetics* 48(6):284–287, (1995).

Schuster et al., "Severe autosomal dominant hypertension and brachydactyly in a unique Turkish kindred maps to human chromosome 12", *Nature Genetics* 13(1) 98–100 (1996).

*Primary Examiner*—Karen Cochrane Carlson
(74) *Attorney, Agent, or Firm*—Albert P. Halluin; Viola T. Kung; Howrey Simon Arnold & White, LLP

(57) ABSTRACT

The present invention relates to a hypertonia gene located on chromosome 12p in the genomic region between genome markers AFM338WH5 and D12S1057 and uses of such a gene.

5 Claims, No Drawings

HYPERTONIA GENE

This application is a National Stage of International Application PCT/DE97/00700, filed Apr. 4, 1997; which claims the priority of DE 196 13 606.7, filed Apr. 4, 1996.

FIELD OF THE INVENTION

The present invention is in the field of molecular biology and biochemistry. Specifically, the present invention relates to a hypertonia gene and its use.

BACKGROUND OF THE INVENTION

Hypertonia, i e. high-blood pressure, is one of the most frequent causes of cardiovascular diseases, particularly of apoplexies. Even though it has long been known from investigations made with twins that hypertonia is due to genetic factors, the ethological and pathogenetic factors are still largely unknown at present. Although molecular methods have accelerated the research of hypertonia, particularly with transgenic animals, they also have made clear that hypertonia is a heterogeneous and complex disease that is caused by gene-gene and gene-environment interactions. The search for genes linked to hypertonia has not yet yielded any satisfactory results.

Therefore, it is the object of the present invention to provide a product by which the genetic cause of hypertonia can be investigated.

According to the invention, this is achieved by the subject matter defined in the claims.

SUMMARY OF THE INVENTION

The subject matter of the present invention relates to a gene located on chromosome 12p in the genomic region between genome markers AFM338WH5 and D12S1057, particularly between genome markers D12S1650 and D12S1057.

Applicant has discovered that the diseases hypertonia, brachydactyly, i.e. shortened extremities, and disorders of fibroblast growth in the form of a shortened cell cycle can be inherited jointly in an autosomal dominant fashion. Applicant has found that a gene is responsible for these conditions. The gene is located on chromosome 12p in the genomic region between genome markers AFM338WH5 and D12S1057, particularly between genome markers D12S1650 and Dl2S1057. Applicant discovered these findings in an investigation of a Turkish family, 50% of the members of which suffer from the above diseases. For this purpose, Applicant carried out an exclusion analysis in which conventional genome markers were used which comprise polymorphous regions of the human genome.

DETAILED DESCRIPTION OF THE INVENTION

A gene according to the invention is located on chromosome 12p in the genomic region between genome markers AFM338WH5 and D12S1057, particularly between genome markers D12S1650 and D12S1057. The genome markers are available under database ID: AFM 338WH5, source: J. Weissenbach, Genethon, Database ID: 6DB609807, source: J. Weissenbach, Genethon, and Database ID: GATA-D12S1057, source: CHLC (Cooperative Human Linkage Center), respectively.

The genomic region between genome markers AFM338WH5 and D12S1057 comprises sequences which are present in the below overlapping YAC clones. These YAC clones are described as follows:

| Designation of the YAC clones | insert sizes (kb) | DSM accession number |
| --- | --- | --- |
| CEHPy904D08872 | 1409 | DSM 10624 |
| CEHPy904F03753 | 1339 | DSM 10628 |
| CEHPy904D09922 | 1329 | DSM 10625 |
| CEHPy904F10891 | 569 | DSM 10629 |
| CEHPy904E07955 | 1759 | DSM 10626 |
| CEHPy904C118O5 | 1339 | DSM 10622 |
| CEHPy904H01799 | 1469 | DSM 10630 |
| CEHPy904C12876 | 1509 | DSM 10623 |
| CEHPy904E08884 | 1649 | DSM 10627 |
| CEHPy904B12792 | 1619 | DSM 10620 |
| CEHPy904B08905 | 1699 | DSM 10619 |
| CEHPy904C09917 | 1719 | DSM 10621 |

The YAC clones were deposited with the DSM (*Deutsche Sammlung von Mikroorganismen und Zellikulturen*GmbH, Mascheroder Weg 1b, D-38124 Braunschweig, [German-type collection of micro-organisms and cell cultures]) under the indicated DSM accession numbers on Mar. 29, 1996. Furthermore, reference is made to Albertsen et aL, *PNAS*, U.S.A., 87:4256–4260 (1990), The preferred genomic region between the genome markers D12S1650 and D12S1057 comprises sequences which are present in the above overlapping YAC clones DSM 10624, DSM 10628, DSM 10625, DSM 10629, DSM 10627, DSM 10620, DSM 10619 and DSM 10621. Particularly preferred sequences are present in YAC clones DSM 10619 and DSM 10621. Especially preferred sequences are present in the YAC clone DSM 10621.

A gene according to the invention can further be characterized by carrying out conventional experiments. It is preferred to isolate the genomic DNA of persons suffering from a combination of hypertonia and brachydactyly and having a shortened fibroblast cell cycle. It is particularly preferred for these persons to come from a family also comprising healthy members. An example of such a family is described by Bilginturan N. et al., *J. Med. Genet.* 10:253–259 (1973). The genomic DNA can then be cleaved by the restriction enzyme Sau3AI, and the resulting fragments can be used for establishing a library, e.g. by using the bacteriophage P1 as a vector. Positive clones of the library can be confirmed and characterized by further hybridization with other YAC clones also located in the indicated genomic region (see, Albertsen, supra).

In addition, the positive clones of the library can be used for the transfection of fibroblast cells. Such cells are removed from healthy persons, i.e. those without hypertonia and brachydactyly and with a normal fibroblast cell cycle. It is preferred for these persons to come from the same family from which diseased persons were used as donors for the genomic DNA. By transfection of the fibroblast cells with the positive clones, it is possible to investigate which clones shorten the cell cycle of the fibroblast cells thereby identifying themselves as a gene according to the present invention. This investigation can be made by common methods (e.g., 5-bromo-2'-deoxy-uridine labeling and detection kit III, Cat. No. 1444611, Boehringer Mannheim). The identified clones can be sequenced and their structure can be elucidated. By this procedure, it is possible to isolate a gene according to the present invention.

A gene according to the invention can be cloned, particularly into expression vectors. A person skilled in the art is familiar with examples of suitable expression vectors. In the case of an expression vector for *E. coli* these are e.g. pGEMEX, pUC derivatives, pGEX-2T, pET3b and pQE-8. For expression in yeast, e.g. pY100 and Ycpadl are particularly suitable while e.g. pKCR, pEFBOS, cDM8 and pCEV4 are particularly suitable for expression in animal cells. The baculovirus expression vector pAcSGHisNT-A is especially suitable for expression in insect cells. A person skilled in the art knows suitable cells to express a gene according to the invention as present in expression vectors. Examples of such cells comprise the *E. coli* strains HB101, DH1, x1776, JM101, JM109, BL21 and SF13009, the yeast strain *Saccharomyces cerevisiae*, the animal cells L, 3T3, FM3A, CHO, COS, Vero and HeLa as well as the insect cells sf9.

A person skilled in the art knows how to insert a gene according to the invention in expression vectors. A gene according to the invention can be inserted in combination with other DNAs coding for further proteins, so that the gene can be expressed in the form of a fusion protein.

Moreover, a person skilled in the art knows conditions of culturing transformed cells and transfected cells, respectively. Moreover, a person skilled in the art is also familiar with processes of isolating and purifying the protein expressed by the gene according to the invention.

In addition, a person skilled in the art knows processes of preparing antibodies against the above protein. Such antibodies may be polyclonal and monoclonal, respectively. For their preparation it is favorable to immunize animals—particularly rabbits or chickens, for polyclonal antibodies and mice for monoclonal antibodies—with the above protein or with fragments thereof. Further boosters of the animals can be effected with the same protein or with fragments thereof. Polyclonal antibodies can then be obtained from the animal serum and egg yolk, respectively. For the preparation of monoclonal antibodies, animal spleen cells are fused with myeloma cells.

As used herein, the term "gene" is understood to mean both DNA sequences and RNA sequences.

By means of the present invention, it is possible to investigate the genetic causes of hypertonia, particularly essential or neurovascular hypertonia. In addition, the present invention provides a means to develop products that can be used for diagnostic measures in the diseases. Such products include, e.g. nucleic acids, particularly DNA and RNA, that are derived from the gene of the present invention and may be used for the detection of the gene and mutations thereof, respectively. Such a detection can be achieved by common DNA and/or RNA determination tests. The results of these tests serve for making predictions on the pathogenesis and disease process, respectively, particularly the apoplexy risks. The results may also form the basis for developing products that can be used therapeutically in these diseases.

What is claimed is:

1. An isolated hypertonia gene, wherein the gene is located on chromosome 12p in the genomic region between genome markers AFM338WH5 and D12S1057.

2. The gene according to claim 1, wherein the genomic region comprises sequences of the overlapping YAC clones DSM 10619, DSM 10620, DSM 10621, DSM 10622, DSM 10623, DSM 10624, DSM 10625, DSM 10626, DSM 10627, DSM 10628, DSM 10629, and DSM 10630.

3. The gene according to claim 1 or 2, wherein that the genomic region comprises sequences of the overlapping YAC clones DSM 10619, DSM 10620, DSM 10621, DSM 10624, DSM 10625, DSM 10627, DSM 10628, and DSM 10629.

4. The gene according to claim 1 or 2, wherein the genomic region comprises sequences of the overlapping YAC clones DSM 10619 and DSM 10621.

5. The gene according to claim 1 or 2, wherein the genomic region comprises sequences of the YAC clone DSM 10621.

* * * * *